(12) United States Patent
Mann et al.

(10) Patent No.: US 8,641,778 B2
(45) Date of Patent: Feb. 4, 2014

(54) PROSTHESIS ATTACHMENT METHOD AND APPARATUS WITH SOFT TISSUE INTEGRATING SEAL

(75) Inventors: Alfred E. Mann, Las Vegas, NV (US); Byron L. Moran, Santa Barbara, CA (US); Abram D. Janis, Valencia, CA (US); Paul Kaluzniak, St. Paul, MN (US)

(73) Assignee: The Alfred E. Mann Foundation for Scientific Research, Santa Clarita, CA (US)

( * ) Notice: Subject to any disclaimer, the term of this patent is extended or adjusted under 35 U.S.C. 154(b) by 0 days.

(21) Appl. No.: 12/735,452

(22) PCT Filed: Jan. 21, 2009

(86) PCT No.: PCT/US2009/000415
§ 371 (c)(1),
(2), (4) Date: Aug. 31, 2010

(87) PCT Pub. No.: WO2009/094166
PCT Pub. Date: Jul. 30, 2009

(65) Prior Publication Data
US 2011/0029002 A1 Feb. 3, 2011

Related U.S. Application Data

(60) Provisional application No. 61/011,918, filed on Jan. 22, 2008.

(51) Int. Cl.
*A61F 2/78* (2006.01)
(52) U.S. Cl.
USPC .............................. 623/32; 606/62

(58) Field of Classification Search
USPC .......................... 623/27–28; 606/54, 62, 310
See application file for complete search history.

(56) References Cited

U.S. PATENT DOCUMENTS

| | | |
|---|---|---|
| 5,098,434 A | 3/1992 | Serbousek |
| 5,360,448 A | 11/1994 | Thramann |
| 5,665,118 A | 9/1997 | LaSalle et al. |
| 5,989,027 A | 11/1999 | Wagner et al. |
| 6,168,633 B1 | 1/2001 | Shoher et al. |
| 6,197,065 B1 | 3/2001 | Martin et al. |
| 6,508,841 B2 | 1/2003 | Martin et al. |
| 6,869,450 B2 * | 3/2005 | Grundei .......................... 623/32 |
| 7,083,648 B2 | 8/2006 | Yu et al. |

(Continued)

FOREIGN PATENT DOCUMENTS

| | | |
|---|---|---|
| EP | 1574174 A1 | 9/2005 |
| WO | WO 0105325 A1 | 1/2001 |
| WO | WO 2005084577 A1 | 9/2005 |
| WO | WO 2006065205 A1 | 6/2006 |

OTHER PUBLICATIONS

PCT International Preliminary Examination Report dated Jul. 27, 2010 in PCT App. No. PCT/US2009/000415.

*Primary Examiner* — Bruce E Snow
(74) *Attorney, Agent, or Firm* — Henricks, Slavin & Holmes LLP

(57) ABSTRACT

A method and apparatus for reducing the incident of infection proximate to an exit site where a prosthesis fastener, e.g., a bone screw, percutaneously penetrates a patient's skin/soft tissue. Infection reduction is achieved in accordance with the invention by growing a tissue integrating seal around the fastener proximate to the exit site.

11 Claims, 3 Drawing Sheets

(56) References Cited

U.S. PATENT DOCUMENTS

| | | |
|---|---|---|
| 2004/0204686 A1 | 10/2004 | Porter et al. |
| 2005/0025656 A1 | 2/2005 | Bhaduri et al. |
| 2005/0032025 A1 | 2/2005 | Bhaduri et al. |
| 2006/0111792 A1 | 5/2006 | Shannon |

\* cited by examiner

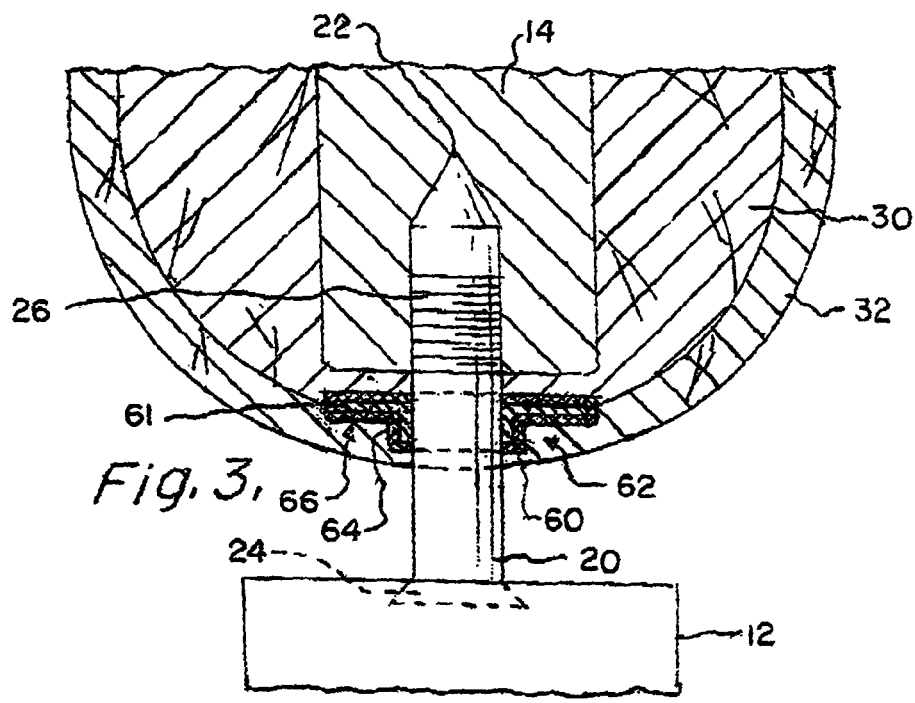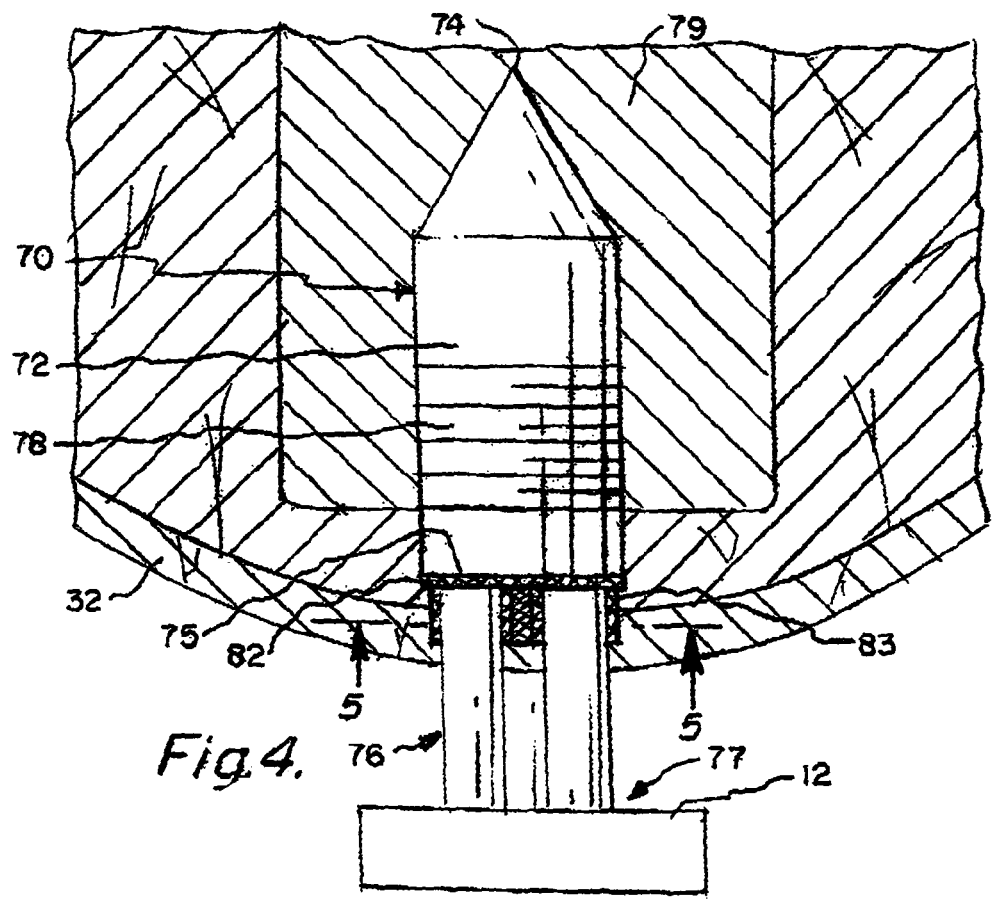

PROSTHESIS ATTACHMENT METHOD AND APPARATUS WITH SOFT TISSUE INTEGRATING SEAL

CROSS-REFERENCE TO RELATED APPLICATIONS

This application is the U.S. national phase under 35 U.S.C. §371 of PCT International Application No. PCT/US2009/000415, which has an International filing date of Jan. 21, 2009, and claims the benefit of U.S. Provisional Application No. 61/011,918, filed Jan. 22, 2008.

FIELD OF THE INVENTION

This invention relates generally to medical technology and more particularly to a method and apparatus for minimizing marsupialization, i.e., pouch formation, and infections associated with the percutaneous projection of a fastener, e.g., bone screw, used to attach a prosthesis.

BACKGROUND OF THE INVENTION

Various techniques are known for attaching a prosthesis to a patient's natural bone. Such techniques often involve the use of a screw having a head end adapted to be secured to the prosthesis and a point end adapted to be threaded or otherwise fixed into the patient's bone. To achieve reliable initial and long term fixation, it has been proposed, e.g., U.S. Pat. No. 5,360,448, to apply a porous coating to the screw shaft designed to accept bone ingrowth.

In an exemplary application, the screw head can be secured to a leg prosthesis and the screw point can be threaded into the patient's thigh bone, or femur. In such, and similar applications, the screw shaft projects percutaneously through the patient's outer skin layers and subcutaneous soft tissue. Over time, these skin layers grow over the natural bone but frequently produce sinus tracts around the screw shaft which are prone to marsupialization and infection, and which can lead to serious cases of osteomyelitis.

U.S. application US2004/0204686 A1 published 14 Oct. 2004, incorporated herein by reference, describes a use of porous material carried on a percutaneously projecting stud of an implantable device for promoting tissue ingrowth to avoid the formation of sinus tracts, form an infection and marsupialization resistant barrier, and enhance device anchoring.

SUMMARY OF THE INVENTION

The present invention is directed to a method and apparatus for reducing the incidence of marsupialization and infection proximate to an exit site where a prosthesis fastener, e.g., a bone screw, percutaneously penetrates the patient's skin/soft tissue. Marsupialization and infection reduction is achieved in accordance with the invention by growing a tissue integrating seal around the fastener proximate to the exit site.

An apparatus in accordance with the invention includes a fastener having a shaft extending between a first end adapted to be secured to a patient's bone and a second end adapted to be secured to an external prosthesis. In accordance with the invention, one or more bands, or layers, of porous material are mounted around the fastener shaft in a position to contact the patient's outer skin layers and subcutaneous soft tissue when the fastener is installed in the patient's bone. The band of porous material, preferably titanium mesh, promotes skin/soft tissue ingrowth which, over time, forms a seal, or barrier, to prevent the incursion of pathogens around the shaft into the patient's body. The seal thus serves to minimize the risk of infections.

A porous band in accordance with the invention preferably comprises multiple fibrous layers of biocompatible materials such as metals, including titanium, nitinol, silver, and stainless steel, etc. or polyolefins including Teflon, nylon, Dacron, and silicone, etc. The fibrous layers can be directly wound onto a portion of the fastener shaft and attached thereto by a suitable technique, e.g., adhesives, welding, brazing, etc. Alternatively, the porous band can be separately fabricated, e.g., of fibrous or sintered metallic or polymeric material, and then attached to the fastener shaft either mechanically or by a suitable adhesion technique including adhesives, welding, brazing, etc. To properly promote skin/soft tissue ingrowth, the porous band preferably has a porosity within a range of 60 to 95% and contains pores within a size range of 50 to 200 microns.

In a preferred embodiment of the invention, the material forming the porous band incorporates appropriate substances to promote healing, reduce inflammation, and resist infection. These functions are particularly important in the initial period after fastener implantation to promote tissue ingrowth into the porous band.

BRIEF DESCRIPTION OF THE FIGURES

FIG. 3 is a side sectional view showing a third embodiment in which the band is configured to provide perpendicular porous surfaces for enhancing tissue integration;

FIG. 4 is a side sectional view showing a fourth embodiment in which the bone screw major shaft transitions into multiple minor shafts for attaching a limb prosthesis to a patient's bone;

DETAILED DESCRIPTION

Figure 1:
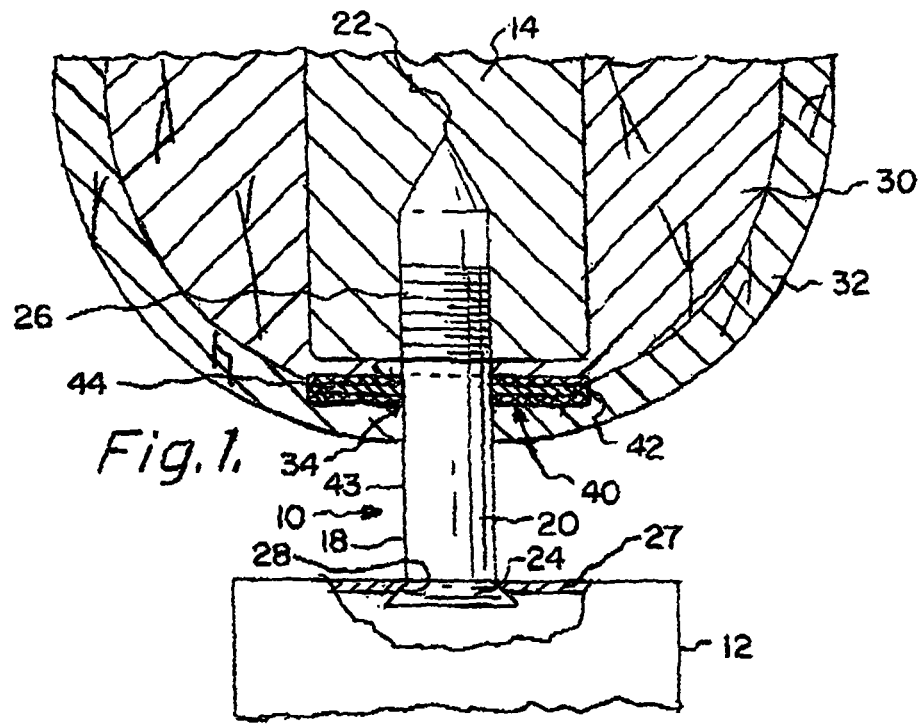
FIG. 1 is a side sectional view showing a bone screw carrying a porous band in accordance with a first embodiment of the invention for attaching a limb prosthesis to a patient's bone, e.g., femur.

Attention is initially directed to FIG. 1 which illustrates a fastener 10 for attaching an external prosthesis 12 to a patient's natural bone 14. Although the teachings of the invention are applicable to a variety of external limb prosthesis devices, in the exemplary application assumed herein, the prosthesis 12 comprises a leg prosthesis and the patient's bone 14 comprises a thigh bone, or femur.

The fastener 10 can comprise a substantially conventional bone screw 18 having a shaft 20 extending between a first, or point end, 22 and a second, or head end, 24. The shaft 20 is appropriately threaded 26 for screwing into the bone 14. The prosthesis 12 is schematically illustrated only to the extent necessary to represent that the head end 24 is configured for attachment to a prosthesis plate 27, e.g., by being seated in prosthesis recess 28 or being otherwise affixed, as by welding or bolting.

Note in FIG. 1 that the fastener 10 projects percutaneously through the patient's subcutaneous soft tissue 30 and outer skin 32 layers. There is significant risk of infection when conventionally implanting a percutaneous screw into a patient's bone because the skin can grow longitudinally along the shaft such that sinus tracts and infections can develop around the percutaneous penetration site. To reduce the risk of infection, a tissue integrating seal 34 is formed in accordance with the invention at the penetration site.

More particularly, in accordance with the invention, a band 40 of porous material 42 is mounted on the shaft 20 longitudinal surface 43 at a location to contact the soft tissue 30 and outer skin 32 when the fastener 10 is fully threaded into bone 14. The porous band 40 preferably formed around a stiff core member 44, e.g., a flange or other appendage to shaft 20, is configured to promote the ingrowth of outer skin and/or soft tissue into its pores. In order to effectively do this, the porous material 42 preferably has a porosity in the range of 60 to 95% and pores within a size range of 50 to 200 microns.

The porous band 40 is preferably formed of material wrapped around core member 44. Alternatively, the band 40 can be separately fabricated and then mounted and affixed to the shaft. The band 40 is preferably formed of a fibrous and/or sintered metal, material, e.g., a suitable biocompatible metal such as titanium, nitinol, nickel, platinum, silver, tantalum, or stainless steel. Alternatively, a polyolefin such as Teflon, nylon, Dacron, or silicone can be used. The band 40 can be affixed to the shaft 20 by various mechanical means and/or suitable adhesion techniques such as welding, brazing, adhesives, etc.

Figure 2:
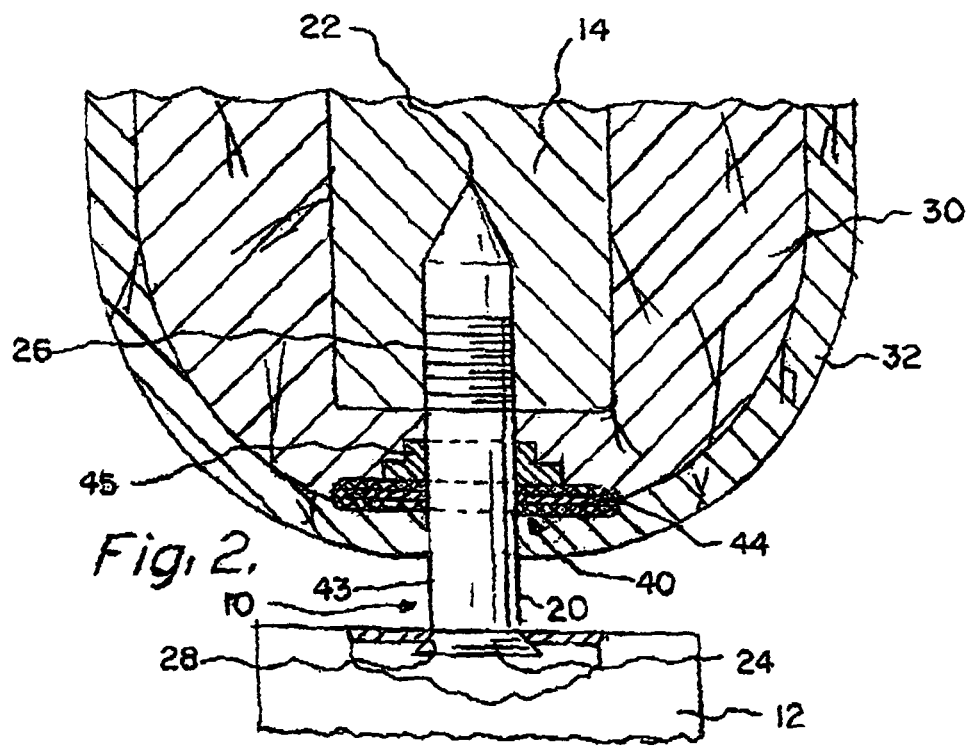
FIG. 2 is a side sectional view showing a second embodiment of the invention including a flange carried on the screw shaft for positioning the porous band.

FIG. 2 illustrates an alternative embodiment in which the shaft 20 carries a mounting flange 45. The flange 45 can be fixedly or adjustably mounted on the shaft 20 to facilitate positioning of the porous band 40 along the shaft longitudinal surface 43. Additionally, the flange 45 provides structural support for the porous band 40.

Attention is now directed to FIG. 3 which is similar to FIG. 1 but shows a modified porous band 60. The porous band 60 is wrapped around core member 61 to form a step 62 to define both a longitudinally oriented porous surface 64 and a laterally oriented porous surface 66. The provision of perpendicular porous surfaces 64, 66 helps to facilitate the growth of an optimally integrated tissue seal around the shaft. The porous band 60 can of course also be advantageously used with the flange 45 of FIG. 2.

Figure 5:
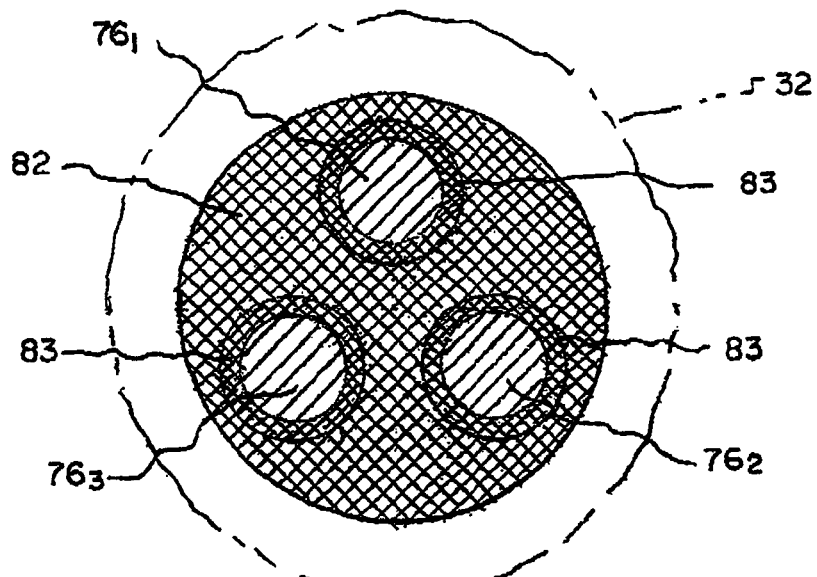
FIG. 5 is a bottom sectional view taken substantially along the plane 5-5 of FIG. 4.

Attention is now directed to FIGS. 4 and 5 which illustrate a specially configured bone screw 70 having a major shaft 72 extending between a first, or bone end 74 and a lateral surface 75. Multiple minor shafts 76 extend from the lateral surface 75 to a second, or prosthesis end 77. The major shaft 72 is appropriately threaded at 78 for screwing into the bone 79. By transitioning the major shaft 72 into multiple smaller shafts 76, (FIG. 5, 76$_1$, 76$_2$, 76$_3$), the screw 70 can be attached to an external prosthesis with less trauma to the surrounding tissue. In the embodiment of FIGS. 4 and 5, porous material 82 is preferably affixed to the lateral surface 75 and additionally porous material 83 is mounted along the longitudinal surfaces of minor shafts 76.

Figure 6:
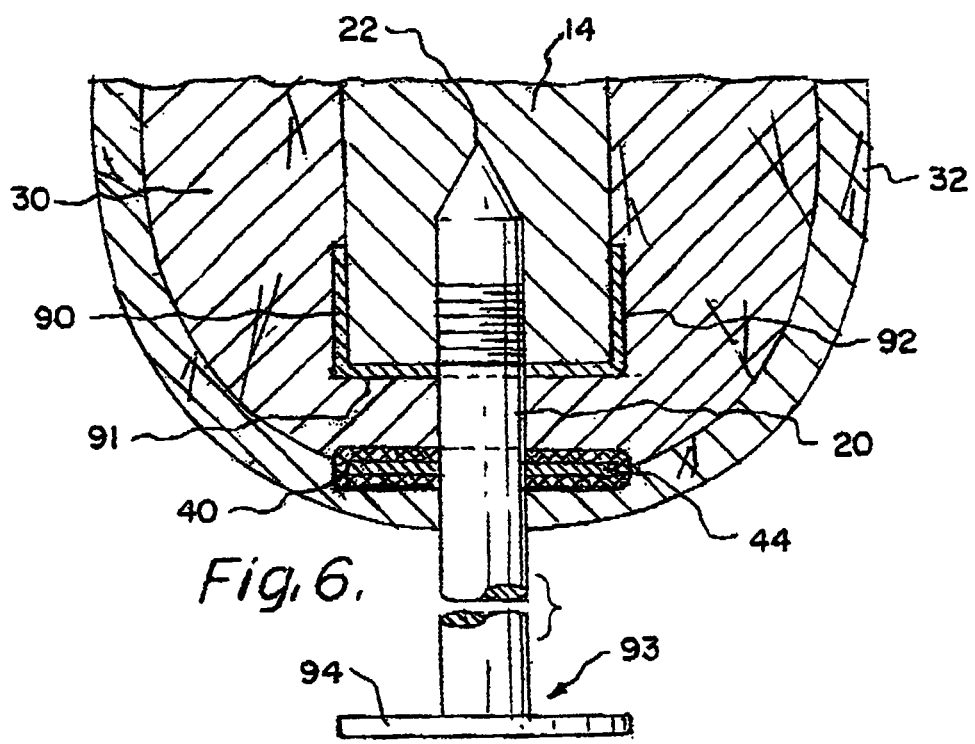
FIG. 6 is a side sectional view showing a fifth embodiment incorporating bone support members.

Attention is now directed to FIG. 6 which shows a further alternative embodiment wherein the shaft 20 carries a bone supporting structural member 90 (e.g. a cup or multiple prongs). The structural member 90 is preferably comprised of lateral support elements 91 and/or longitudinal support elements 92 for bearing against the periphery of bone 14 to support and strengthen the bone to avoid cracking. FIG. 6 also shows shaft 20, affixed at its lower end 93 to a plate 94 configured for attachment to the external prosthesis.

From the foregoing, it should be clear that a method and apparatus have been described for attaching a prosthesis to a patient's bone. The method and apparatus utilize a bone fastener carrying a band of porous material for promoting skin and soft tissue ingrowth to form a barrier around the fastener shaft for minimizing the risk of marsupialization and infection. The porous material preferably has a porosity in the range of 60 to 95% and pore size in the range of 50 to 200 microns. Although only a limited number of embodiments have been disclosed, it is recognized that various modifications will occur to those skilled in the art which fall within the intended scope of the appended claims.

The invention claimed is:

1. A fastener for attaching an external prosthesis to a patient's bone comprising:
    an elongated fastener configured for percutaneous implantation having a shaft extending from a first end adapted for attachment to a patient's bone to a second end configured for attachment to an external prosthesis, the shaft including a major shaft portion, defining a longitudinal axis, adjacent to said first end, and multiple minor shaft portions adjacent to said second end, said minor shaft portions being adapted for attachment to an external prosthesis and defining respective longitudinal axes that are radially offset from the longitudinal axis of the major shaft portion; and
    a band of porous material mounted on said shaft located to contact a patients subcutaneous soft tissue, said porous material having a porosity suitable for promoting skin and soft tissue ingrowth.

2. The fastener of claim 1 wherein said porous material is comprised of a metal from a group including titanium, nitinol, nickel, platinum, silver, tantalum and stainless steel.

3. The fastener of claim 1 wherein said porous material is comprised of a polyolefin from a group including Teflon, nylon, Dacron, and silicone.

4. The fastener of claim 1 wherein said porous material comprises a mesh of fibrous material.

5. The fastener of claim 1 wherein said porous material comprises a mass of sintered metal material.

6. The fastener of claim 1 wherein said porous material incorporates an agent for promoting tissue healing and/or resisting infection and inflammation.

7. The fastener of claim 1 wherein
    said band of porous material includes a longitudinally extending porous surface extends a first distance in the longitudinal direction and laterally extending porous surfaces that are transverse to the longitudinal axis of the shaft major portion and extend a second distance in the transverse direction, the second distance being greater than the first distance.

8. The fastener of claim 1 wherein said band of porous material has a porosity within a range of 60 to 95% and pores within a size range of 50 to 200 microns.

9. The fastener of claim 1 wherein said porous material is formed around a stiff core.

10. The fastener of claim 1 further including at least one structural member attached to said shaft for bearing against the periphery of said bone.

11. The fastener of claim 10, wherein
    said at least one structural member includes one or more support members extending laterally and longitudinally.

* * * * *